United States Patent
Kladders

(10) Patent No.: US 8,205,613 B2
(45) Date of Patent: Jun. 26, 2012

(54) PISTON DOSING PUMP

(75) Inventor: Heinrich Kladders, Muelheim/Ruhr (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 570 days.

(21) Appl. No.: 12/441,182

(22) PCT Filed: Aug. 17, 2007

(86) PCT No.: PCT/EP2007/007270
§ 371 (c)(1),
(2), (4) Date: Jun. 18, 2009

(87) PCT Pub. No.: WO2008/034506
PCT Pub. Date: Mar. 27, 2008

(65) Prior Publication Data
US 2010/0024815 A1 Feb. 4, 2010

(30) Foreign Application Priority Data

Sep. 20, 2006 (DE) .......................... 10 2006 044 752

(51) Int. Cl.
*A61M 15/00* (2006.01)
*A61M 16/00* (2006.01)
*B05D 7/14* (2006.01)
*B65D 83/06* (2006.01)

(52) U.S. Cl. .............................. 128/203.15; 128/203.19

(58) Field of Classification Search ............. 128/203.12, 128/203.15, 203.19, 203.23, 203.24; 222/361, 222/630–631, 634, 636; 141/67, 249, 260; 414/219–220, 304, 323; *A61M 15/00, 16/00; B05D 7/14; B65D 83/06*
See application file for complete search history.

(56) References Cited

U.S. PATENT DOCUMENTS

| | | | |
|---|---|---|---|
| 3,244,328 A | 4/1966 | Brown | |
| 5,113,855 A * | 5/1992 | Newhouse | 128/203.12 |
| 5,201,308 A * | 4/1993 | Newhouse | 128/203.15 |
| 5,239,992 A | 8/1993 | Bougamon et al. | |
| 5,341,801 A * | 8/1994 | Zechner | 128/203.15 |
| 5,503,144 A * | 4/1996 | Bacon | 128/203.15 |
| 5,568,884 A * | 10/1996 | Bruna | 222/189.09 |
| 5,634,900 A | 6/1997 | Makino et al. | |
| 7,708,011 B2 | 5/2010 | Hochrainer et al. | |

(Continued)

FOREIGN PATENT DOCUMENTS

CA 2 090 227 C 3/1992

(Continued)

OTHER PUBLICATIONS

International Search Report for PCT/EP2007/007270 mailed Nov. 28, 2007.

*Primary Examiner* — Oren Ginsberg
(74) *Attorney, Agent, or Firm* — Michael P. Morris; David L. Kershner

(57) ABSTRACT

A preferably pulverulent formulation to be dosed is received in a dosing chamber having a partly gas-permeable wall. The introduction and discharge of the formulation is achieved by means of a pumping device that alternately generates a negative pressure and an excess pressure in the dosing chamber. The dosing chamber can also be displaced between a receiving position and a discharge position by means of a piston, the piston controlling the negative and excess pressure in the dosing chamber. Furthermore, the size of the dosing chamber is adjustable.

20 Claims, 4 Drawing Sheets

U.S. PATENT DOCUMENTS

| | | |
|---|---|---|
| 7,870,856 B2 | 1/2011 | Boeck |
| 7,984,713 B2 | 7/2011 | Hochrainer et al. |
| 2004/0187868 A1 | 9/2004 | Hochrainer et al. |
| 2005/0263151 A1 | 12/2005 | Hochrainer et al. |
| 2007/0240713 A1 | 10/2007 | Boeck |
| 2009/0194105 A1 | 8/2009 | Besseler et al. |
| 2009/0235929 A1 | 9/2009 | Egen et al. |
| 2010/0024815 A1 | 2/2010 | Kladders |
| 2011/0203586 A1 | 8/2011 | Egen et al. |

FOREIGN PATENT DOCUMENTS

| | | |
|---|---|---|
| DE | 40 27 391 A1 | 3/1992 |
| EP | 0 516 510 A1 | 2/1992 |
| EP | 0 546 996 A2 | 6/1993 |

* cited by examiner

PISTON DOSING PUMP

This application is the national phase entry under 35 U.S.C. §371 of International Application No. PCT/EP2007/007270, filed Aug. 17, 2007, which claims priority to German Application No. 10 2006 044 752.2, filed Sep. 20, 2006, each of which is hereby incorporated by reference in its entirety.

The present invention relates to a dosing device, preferably for an inhaler, for dosing a a small amount of an in particular powdered formulation, having a reservoir (3) for the formulation (2), having a dosing chamber (7) for receiving formulation (2) supplied from the reservoir (3), wherein the dosing chamber (7) has a wall (8) that is gas-permeable at least in parts, so that the formulation (2) can be taken into the dosing chamber (7) by underpressure or an air current and can be expelled from the dosing chamber (7) by overpressure or an air current, and a inhaler comprising such a dosing device and a method of dosing a small amount of an in particular powdered formulation.

The present invention relates in particular to an inhaler for the delivery or inhalation of a preferably powdered formulation, i.e. a powder inhaler. However, the formulation may theoretically also be in liquid phase, a dispersion or in some other fluidisable form.

The formulation is, in particular, a therapeutic agent or medicament. In particular, the formulation accordingly contains at least one active substance or consists thereof. The formulation thus serves particularly for medical treatment or other therapeutic purposes.

By the phrase "small amount" is meant in the present invention preferably a volume of about 0.1 to 25 µl, more particularly up to 10 µl, and/or a weight of 0.1 to 25 mg, more particularly up to 10 mg.

U.S. Pat. No. 4,350,094 discloses a dosing device for dosing a small amount of a formulation. A dosing chamber is bounded by walls of porous material and is arranged at the end of a tubular carrier. The formulation to be dosed can be sucked into the dosing chamber by underpressure. The formulation can be expelled from the dosing chamber again by the use of overpressure or compressed air.

DE 40 27 391 A1 discloses a propellant-free inhaler having a dosing device for dosing and delivering a powdered formulation. The dosing is carried out by means of a band or ribbon which pulls the formulation out of a dosing chamber into an inhalation channel. The formulation is then expelled by means of an extraneous air current produced by the inhaler.

The aim of the present invention is to provide a dosing device, preferably for an inhaler, an inhaler having such a dosing device and a method of dosing a small amount of the formulation, wherein a simple compact structure, easy operation, highly accurate dosing and/or optimum adaptability or universal usability are made possible.

The above objective is achieved by means of a dosing device according to claim 31, or by a method according to claim 51. Advantageous further features are the subject matter of the subsidiary claims.

In a first aspect of the present invention, a reduced pressure or air current for picking up or taking in the formulation into the dosing chamber and an overpressure or air current for expelling the formulation from the dosing chamber are produced alternately by means of a pumping device. This provides a simple, compact and inexpensive construction and easy operation or activation.

According to a second aspect of the present invention a piston is provided which carries or forms the metering chamber and which is movable between an uptake position for taking up the formulation and a delivery position for delivering the formulation. This allows optimum dosing while retaining a simple and compact structure.

By the term "piston" is meant in particular an elongate or rod-shaped, preferably cylindrical element. However, in a broader sense it may also refer to any other movable element. In particular, the element is constructed as a valve element or control element.

Particularly preferably, as a result of the movement of the dosing chamber between the uptake position and the delivery position and/or as a result of the reverse movement, there is a control of the underpressure and/or overpressure or the air currents for taking the formulation into the dosing chamber and/or expelling the formulation from the dosing chamber. This allows particularly easy operation and a simple, compact and inexpensive construction.

In a third aspect of the present invention, the size of the dosing chamber is adjustable. This is advantageous for achieving a desired dosage with a simple construction.

The proposed dosing device may theoretically be used for various purposes. Most preferably, an inhaler has a proposed dosing device. Accordingly, a simple, compact and inexpensive construction of the inhaler is obtained while achieving high dosing accuracy.

In the present invention the terms "air" and "air current" are preferably also to be understood in the broader sense as encompassing a different gas or a current of such a gas. However, the term "air" is used throughout in the following description as it usually air that is used as the gas and conveying medium for the dosing and optionally also the conveying of the formulation.

Further aspects, features, properties and advantages of the present invention will become apparent from the claims and the following description of some preferred embodiments by reference to the drawings.

Figure 1:
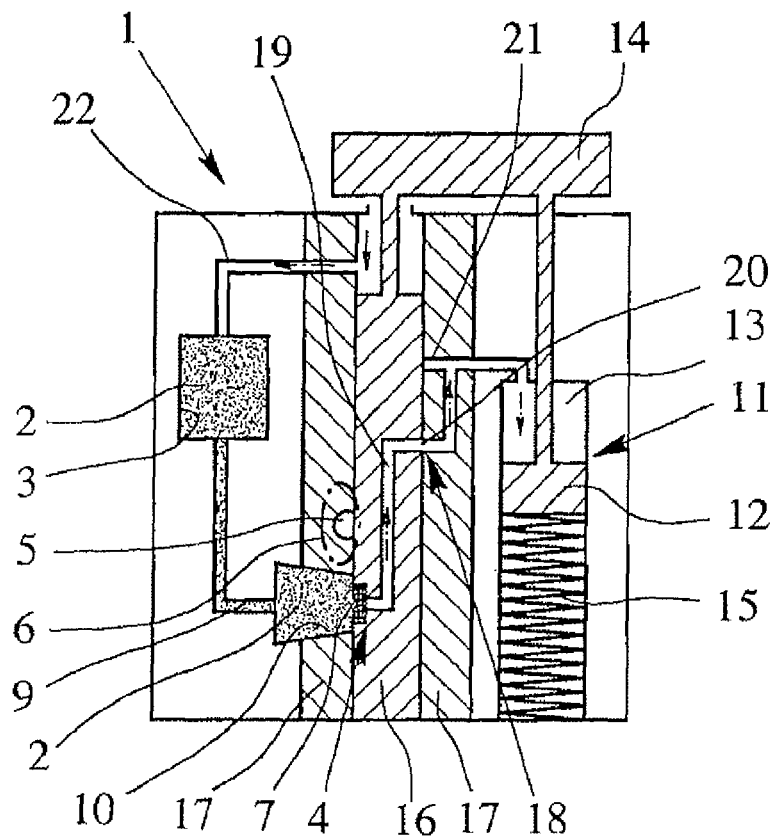
FIG. 1 a schematic section through an inhaler according to a first embodiment during dosing.

In the figures, the same reference numerals have been used for identical or similar parts, even if the associated description has been omitted. In particular, the same or corresponding advantages and properties are then obtained. For reasons of simplicity or clarity the individual figures are not to scale and have been reduced to the essential components relevant to the invention.

FIG. 1 diagrammatically shows the construction of a proposed inhaler 1 according to a first embodiment. The inhaler 1 is preferably of portable design and/or operates purely mechanically, in particular.

The inhaler serves for the delivery or inhalation of a preferably powdered formulation 2 in the sense described above.

In the embodiment shown the formulation 2 is present in bulk or loose form, in particular. The formulation 2 is accommodated, in particular, in a reservoir 3 or the like.

The inhaler 1 further comprises a proposed dosing device 4 for dosing the formulation 2 in small amounts in the sense described above. In particular dosing is carried out one after another or before the next inhalation or dispensing of the formulation 2.

The dosing device 4 in particular forms part of the inhaler 1 or is integrated therein or formed thereby. However, the dosing device 4 may generally also be separable from the inhaler 1. Moreover, the proposed dosing device 4 is theoretically suitable for use for other purposes, in measuring equipment or the like.

The measured out or dosed formulation 2 is preferably expelled or delivered through a delivery channel 5 and in particular an outlet 6 adjoining it, indicated by broken lines here, such as a mouthpiece or the like.

Figure 2:
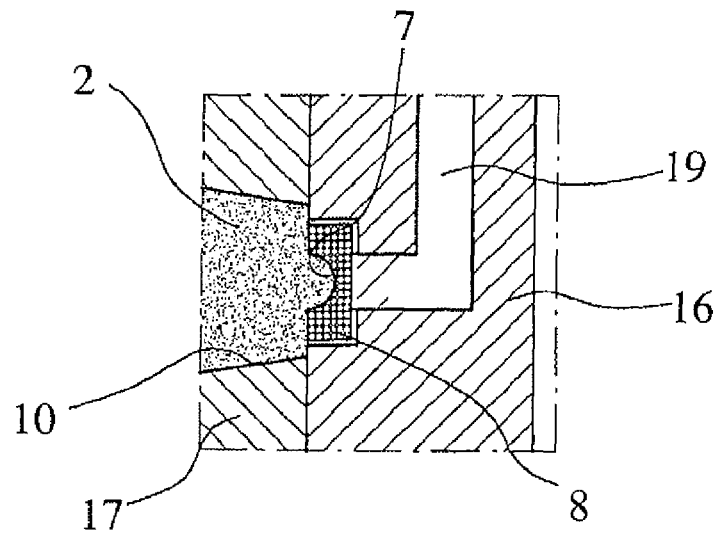
FIG. 2 an enlarged view of a detail from FIG. 1.
Figure 3:
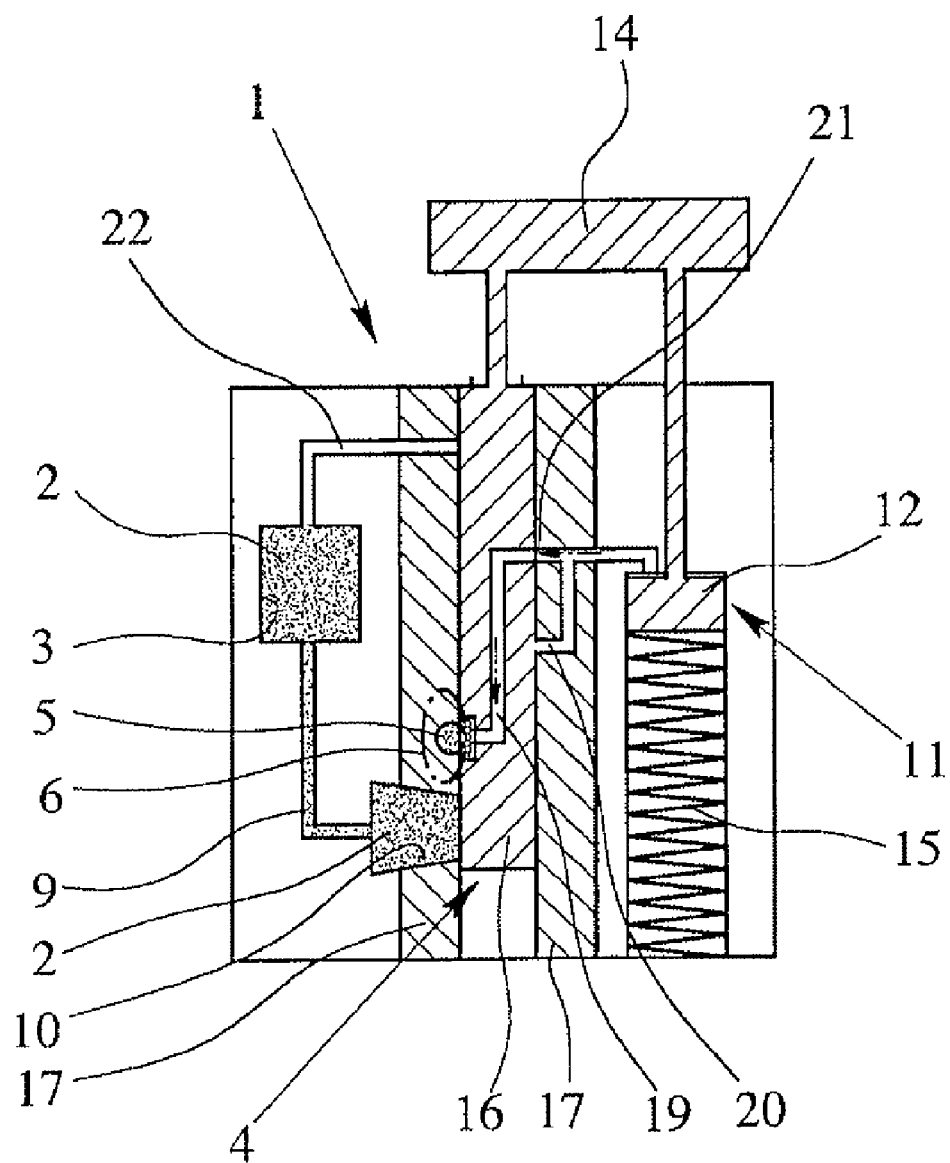
FIG. 3 a schematic section through the inhaler according to FIG. 1 during dispensing.
Figure 4:
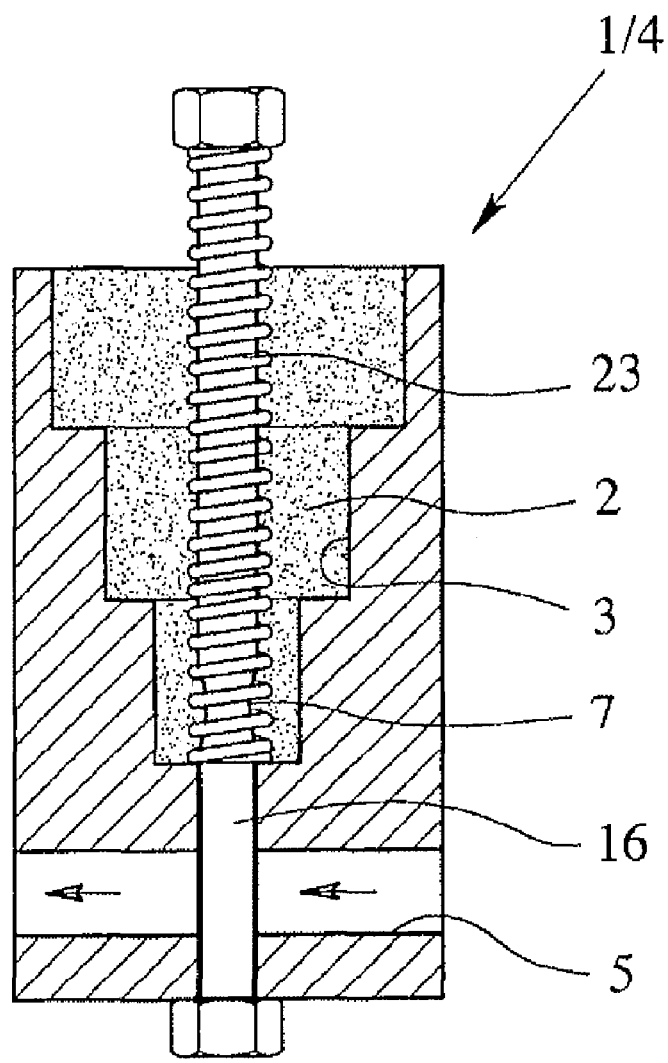
FIG. 4 a schematic section of a detail of an inhaler according to a second embodiment.

FIG. 1 shows the inhaler 1 or dosing device 4 during the measuring out or dosing, particularly during the filling of a dosing chamber 7 of the dosing device 4. FIG. 2 shows in an enlarged detail from FIG. 1 a preferred structure of the dosing chamber 7 and illustrates the filling of the dosing chamber 7. FIG. 3 shows in a schematic section corresponding to FIG. 1 the inhaler 1 or the dosing device 4 during the expulsion of the formulation 2, particularly during the emptying of the dosing chamber 7.

The dosing chamber 7 serves to hold or measure out or dose the formulation 2. The dosing chamber 7 preferably has an at least partially gas-permeable wall 8. In particular, the dosing chamber 7 or wall 8 consists at least in part of porous material, preferably sintered material. Particularly preferably, the dosing chamber 7 is in the shape of a well or pot, as shown in FIG. 2. However, other designs are also possible.

In the embodiment shown, the dosing chamber 7 or wall 8 is preferably formed at least partially, preferably completely, by an insert particularly of porous material. However, other arrangements or designs are also possible. As an example, reference may be made here to U.S. Pat. No. 4,350,049 mentioned hereinbefore.

The formulation 2 can be taken up, in particular by under pressure, from the reservoir 3 in the dosing chamber 7 or by means of an air current into the dosing chamber 7 and particularly sucked into it. In the embodiment shown the formulation 2 can be supplied from the reservoir 3 through an optional feed line 9 and/or an intermediate store or feed chamber 10 to the dosing chamber 7.

The taking up or suction of the formulation 2 by under pressure and optionally even vacuum or by an air current into the dosing chamber 7 or through said chamber ensures particularly effective and defined or total filling of the dosing chamber 7 with the formulation 2. Particularly preferably, the under pressure is applied by sucking air out of the dosing chamber 7 through the porous wall 8. However, the dosing chamber 7 may additionally or alternatively also be filled with the formulation 2 by the effect of gravity and/or other effects.

The delivery of the formulation 2 and/or the emptying of the dosing chamber 7 are preferably carried out by overpressure or an air current from the dosing chamber 7. This allows a very effective, fast and defined or total emptying of the dosing chamber 7. In addition, it assists the dispersion of the formulation 2. In particular, compressed air or the air current is passed through the porous wall 8 into the dosing chamber 7. Additionally or alternatively, the emptying of the dosing chamber 7 may also be assisted or effected by gravity, vibration, impact or other effects.

The inhaler 1 or dosing device 4 comprises a pump device 11 which produces both the underpressure and the overpressure or the respective air currents, preferably alternately. However, the underpressure or air current for filling the dosing chamber 7 and/or the overpressure or air current for emptying the dosing chamber 7 may also be provided or supplied by separate devices and/or a separate device or the like.

In the embodiment shown the pump device 11 comprises a pump piston 12 which is reciprocally movable in a pump chamber 13, particularly by means of an associated actuating device 14 and/or spring 15. In particular, the pump device 11 or actuating device 14 can be operated manually. The optional spring 15 serves to restore the pump piston 12 in the embodiment shown.

In the embodiment shown the pump piston 12 can be moved by means of the actuating device 14 counter to the force of the spring 15 into the position shown in FIG. 1, so that an underpressure can be produced in the pump chamber 13 or air can be sucked into the pump chamber 13. During the opposite movement of the pump piston 12—in particular as a result of the restoring force of the spring 15 after the release of the actuating device 14 or a handle formed thereby or the release of a barrier or the like—into the position shown in FIG. 3, air is forced out of the pump chamber 13 and accordingly an overpressure or air current for emptying the dosing chamber 7 is produced or provided. However, other technical implementations are also possible.

In the embodiment shown, the dosing chamber 7 is movable between an uptake position for taking up the formulation 2 (FIG. 1) and a delivery position for delivering the formulation 2 (FIG. 3) and vice versa. This movement is used in particular to control the underpressure and/or overpressure or corresponding air currents active in the dosing chamber 7.

Preferably the dosing chamber 7 is arranged on or formed or carried by a piston 16 in the sense described hereinbefore. The piston 6 is movable back and forth between the uptake position and delivery position. Particularly preferably, the dosing chamber 7 or the insert that forms the dosing chamber 7 or the like is arranged on the side of the piston 16 and opens particularly to a piston guide 17 which at least partially surrounds the piston 16.

The piston 16 is preferably longitudinally movable in the piston guide 17. The piston guide 17 is provided with the supply means for the formulation 2—with the supply chamber 10 in the embodiment shown—so that in the uptake position (FIGS. 1 and 2) of the piston 16 the formulation 2 can be supplied to the dosing chamber 7, and in particular the laterally open dosing chamber 7 is directly connected to the supply chamber 10 or reservoir 3 or the like which is then adjacent thereto.

In the delivery position the piston 16 has been pushed along so that the dosing chamber 7 communicates with the delivery channel 5 (FIG. 3).

In the embodiment shown the movement of the dosing chamber 7 from the uptake position into the delivery position and vice versa is coupled in particular to the actuation of the pump device 11, particularly preferably by the fact that the piston 16 can also be actuated or moved by means of the actuating device 14. In particular, the piston 16 is fixably connected for this purpose to the actuating device 14 or the handle formed thereby, the same as the pump piston 12 in the embodiment shown. However, other technical solutions are also possible here.

The proposed dosing device 4 or pump device 11 preferably comprises a valve device 18 for controlling when the dosing chamber 7 will be subjected to underpressure and/or overpressure or when the air will be sucked into or out of the dosing chamber 7, in order to deliver the formulation 2 into the dosing chamber 7 or expel the formulation 2 from the dosing chamber 7 or empty the dosing chamber 7.

In the embodiment shown the valve device 18 is preferably formed by the piston 16 or a communication channel 19 in the piston 16 and by a first connecting channel 20 and a second connecting channel 21 in the piston guide 17 or the like. The two connecting channels 20, 21 are connected to the pump chamber 13 and are arranged or offset along the piston guide 17, in accordance with the uptake position and delivery position of the piston 16 or dosing chamber 7, such that preferably a pneumatic connection between the respective connecting channel 20 or 21 on the one hand and the communication channel 19 on the other hand is formed only in the uptake position and delivery position in each case.

The construction described above or some other construction particularly preferably facilitates or results in the following procedure. When the emptied dosing chamber 7 is moved from the delivery position into the uptake position, underpressure is produced in the pump chamber 13. When the dosing chamber 7 then reaches the uptake position, a pneumatic connection is formed between the communication channel 19 and the first connecting channel 20, so that the underpressure prevailing in the pump chamber 13 and at the connecting channels 20, 21 sucks air through the porous wall 8 from the dosing chamber, more particularly in an abrupt or very rapid fashion, and thereby—at least temporarily—produces an underpressure in the dosing chamber 7 and/or an air current from the reservoir 3 or feed chamber 10 into the dosing chamber 7 (as indicated by arrows in FIG. 1), thereby conveying the formulation 2 into the dosing chamber 7 or sucking it in. In this way the dosing chamber 7 is filled very rapidly and completely with the formulation 2, in a defined manner, or this is at least assisted.

In the embodiment shown, the reservoir 3 or the supply chamber 10 is preferably connected to the atmosphere through a supply air channel 22, so that air can flow in through it and thus establish equilibrium with the ambient pressure in the dosing chamber 7 which is now full.

Theoretically, however, it is also possible for the pump device 11 to place the reservoir 3 or the supply chamber 10 containing the formulation 2 under overpressure for filling the dosing chamber 7 with the formulation 2 or to produce an air current into the dosing chamber 7 through the reservoir 3 and/or the supply chamber 10 so that the formulation 2 is conveyed in the desired manner into the dosing chamber 7, the air fed in being able to escape through the porous wall 8 of the dosing chamber 7 or by some other suitable means. Here, too, an air current is also produced for filling the dosing chamber 7 with the formulation 2.

The filled dosing chamber 7 is then moved from the uptake position into the delivery position. In the course of this movement the air contained in the pump chamber 13 is compressed, and in the embodiment shown the pump piston 12 is moved upwards into the position shown in FIG. 3. As a result an overpressure is produced in the pump chamber 13 or in the attached connecting channels 20, 21. Only when the delivery position is reached does the valve device 18 open, producing a pneumatic connection between the second connecting channel 21 and the communication channel 19. The overpressure is able to escape into the dosing chamber 7 through the porous wall 8 and there produce an overpressure or air current which expels the formulation 2 from the dosing chamber 7, particularly into the adjoining delivery channel 5 of the inhaler 1. This is shown by arrows, particularly in FIG. 3.

The air current that causes the dosing chamber 7 to empty also assists the dispersing of the formulation 2, in particular, into very fine particles in the delivery channel 5. In particular, at the same time or immediately after the emptying of the dosing chamber 7 the formulation 2 is delivered through the delivery channel 5 and out through the outlet 6. In particular, an air current is produced as a user (not shown) breathes in or inhales. In addition or alternatively, an air current may be produced by a pump or even by the pump device 11. Alternatively or additionally, the inhaling or breathing in by a user may also only trigger the expulsion of the formulation 2, i.e. form a so-called breath trigger.

The proposed construction provides a very simple, compact and inexpensive design as well as a simple operation and in particular it is necessary only to operate the preferably common actuating device 14.

As a result of the filling and emptying of the dosing chamber 7 by underpressure and overpressure or corresponding air currents, the dosing device 4 or the inhaler 1 operates at least substantially independently of gravity or any spatial orientation, which means that very accurate dosing is possible in any position.

In the embodiment shown the reservoir 3 preferably forms part of the dosing device 4. However, the reservoir 3 may also be formed separately therefrom and/or may be replaceable.

In the embodiment shown the pump device 11 can preferably be operated manually. However, the pump device 11 can theoretically also be operated by some other method, for example electrically. Furthermore, the term "pump device" should preferably be understood in a very broad sense as meaning that it also encompasses any other pressure generation and in general terms the provision of pressurised gas or the like, for example by means of a pressurised container, a cartridge or the like.

The proposed dosing device 4 may be used in particular also for filling capsules or other containers in the dosing of the formulation 2 at the factory, in particular. The predosed capsules or containers are then, in particular, used in a conventional inhaler.

Some additional embodiments of the proposed inhaler 1 or the proposed dosing device 4 will be described below with reference to the highly schematic views in FIGS. 4 and 5 which show only parts of the apparatus. The remarks and explanations given earlier continue to apply accordingly or in a supplementary capacity. However, the embodiments described below may also be used independently thereof in other inhalers or dosing devices or the like.

FIG. 4 shows a second embodiment in a schematic section of a detail. The piston 16 with the dosing chamber 7 preferably extends into the reservoir 3 and more particularly right through it.

The dosing chamber 7 is constructed here in particular as an encircling or annular recess, depression or groove. The filling of the dosing chamber 7 with the formulation 2 takes place in the reservoir 3 preferably by gravity and/or the sliding of the preferably loose supply of formulation 2.

The piston 16 preferably has an associated device for loosening the formulation 2 in the reservoir 3. The loosening device in particular prevents undesirable bridges or other solidified portions of formulation 2 from forming inside the reservoir 3 as the piston 16 is moved. In particular, the device results in the loosening or a certain fluidisation of the formulation 2.

In the embodiment shown the loosening device is preferably formed by a spring 23. This is particularly preferably a restoring spring 23 for returning the piston 16 into the uptake or delivery position. In the embodiment shown the restoring spring 23 biases the piston 16 into the uptake position shown in FIG. 4.

The piston 16 can be pushed out of the uptake position shown in FIG. 4, so that the dosing chamber 7 can be shifted from the reservoir 3 into the associated delivery channel 5, where the formulation 2 picked up from the dosing chamber 7 can be discharged by means of an air current indicated by arrows in the sense described previously or by some other suitable conveying medium. The restoring spring 23 then preferably causes resetting into the uptake position. The movement that takes place as a result (compression and release) of the restoring spring 23 or some other element in the formulation 2 and/or relative to the piston 16 brings about the desired loosening or fluidisation of the formulation 2 in the reservoir 3.

Figure 5:
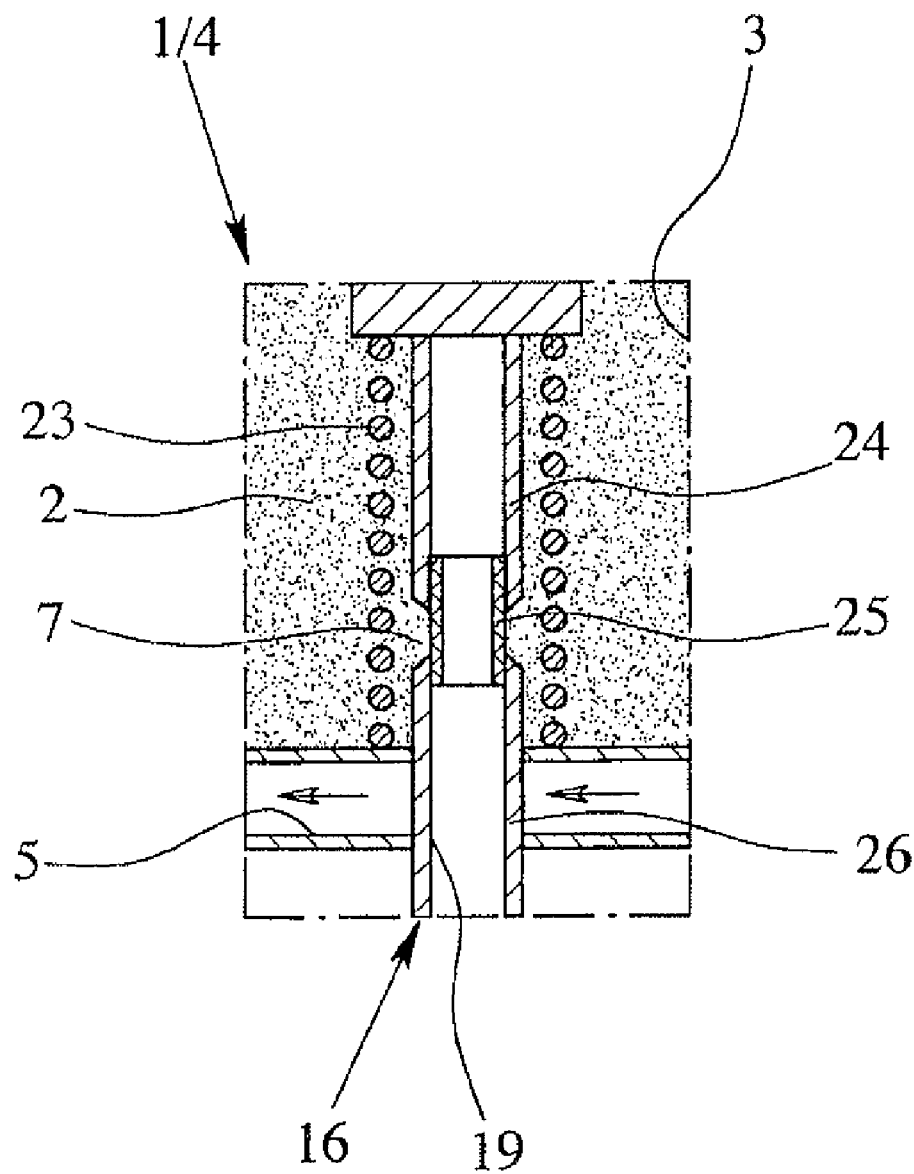
FIG. 5 a schematic section of a detail of an inhaler according to a third embodiment.

FIG. 5 shows in another schematic view of a detail a third embodiment of the proposed inhaler 1 or the proposed dosing device 4. The third embodiment functionally corresponds substantially to the second embodiment, and reference will therefore be made to the associated remarks and explanations. Only major differences will be described hereinafter.

In the third embodiment the size of the dosing chamber 7 is variable. This is made possible in the embodiment shown by the fact that the dosing device 4 has at least two piston or dosing chamber parts 24 and 25 which are movable towards one another, in particular by screwing or turning. In particular, the parts 24 and 25 can be screwed axially into one another. In the embodiment shown, the part 25 is in particular of porous and/or sleeve-like construction and forms the gas-permeable wall 8 of the dosing chamber 7. The part 25 is partially covered by the other part 24, while the size, in this case the axial length, of the dosing chamber 7 can be varied by the degree of overlap.

In the embodiment shown, the preferably gas-permeable part 25 at the other end is connected to another piston or dosing chamber part 26 or formed thereon. In particular, the parts 24 to 26 form the piston 16 and/or define or form the dosing chamber 7.

In order to adjust the size of the dosing chamber 7 or move it, the parts 24 and 25 or the parts 24 and 26 can be rotated relative to one another. This is a very simple way of adapting the dosing device 4 to the desired dosing amount in each case.

In the third embodiment the dosing chamber 7 or the piston 16 is preferably of hollow construction, at least in parts, in order to assist or allow the filling and emptying of the dosing chamber 7 by means of underpressure or overpressure and/or corresponding air currents. In this case the sleeve-like or inner part 25 in particular is of porous construction, for example made of sintered material, in order to achieve the desired gas permeability.

In the embodiment shown the inhaler preferably operates purely mechanically. However, it is theoretically also possible for the inhaler 1 to operate electrically or electronically and/or to comprise such components or parts. This applies particularly to a trigger device for initiating the release of the formulation 2 or for fixing the inhalation time, a drive, a pump, a counter, a lock, a control device or the like.

Individual features and aspects of the different embodiments may also be combined with one another as desired or used in other designs of inhalers.

The present invention is not restricted to inhalers but may also be used accordingly in other atomisers. Therefore, the term "inhaler" is preferably to be taken in a wider sense as meaning that it also encompasses other types of dispensers or atomisers, particularly for medical or other therapeutic purposes.

Some preferred ingredients and/or compositions of the preferably medical formulation 2 are listed below. As already mentioned they consist in particular of powders, or fluids in the broadest sense. Most preferably, the formulation 2 contains:

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl]sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino]ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethylethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1.1dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3.4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]-phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2,6-dichloro-benzyloxy)-ethoxy]-hexylamino}-1-hydroxy-ethyl)-2-hydroxymethyl-phenol 3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide 4-(2-{6-[4-(3-cyclopentanesulphonyl-phenyl)-butoxy]-hexylamino}-1-hydroxyethyl)-2-hydroxymethyl-phenol N-adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

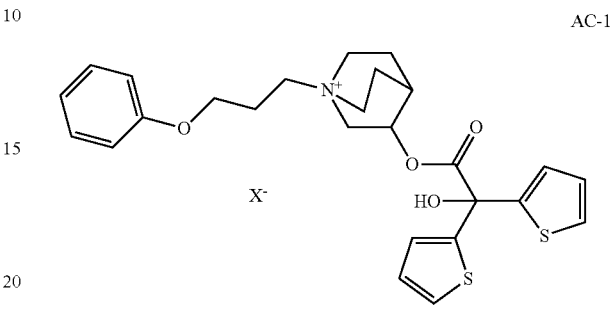

AC-1 wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

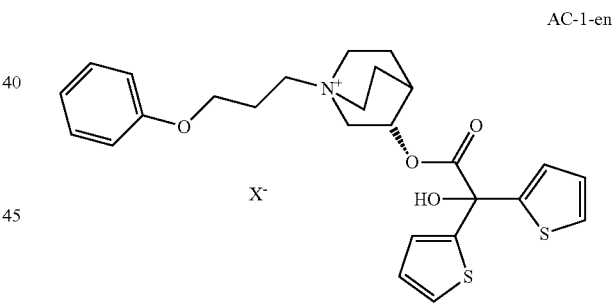

AC-1-en wherein X⁻ may have the above-mentioned meanings. Other preferred anticholinergics are selected from the salts of formula AC-2

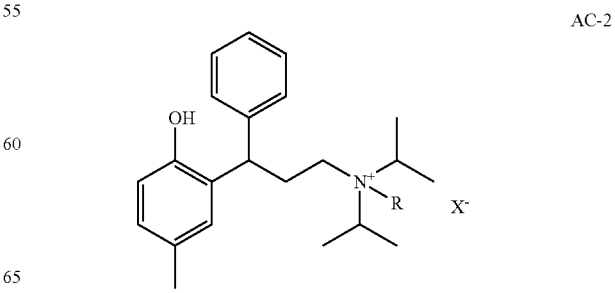

AC-2 wherein R denotes either methyl or ethyl and wherein X⁻ may have the above-mentioned meanings. In an alternative embodiment the compound of formula AC-2 may also be present in the form of the free base AC-2-base.

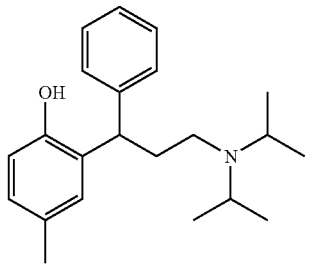

AC-2-base

Other specified compounds are:
- tropenol 2,2-diphenylpropionate methobromide,
- scopine 2,2-diphenylpropionate methobromide,
- scopine 2-fluoro-2,2-diphenylacetate methobromide,
- tropenol 2-fluoro-2,2-diphenylacetate methobromide;
- tropenol 3,3',4,4'-tetrafluorobenzilate methobromide,
- scopine 3,3',4,4'-tetrafluorobenzilate methobromide,
- tropenol 4,4'-difluorobenzilate methobromide,
- scopine 4,4'-difluorobenzilate methobromide,
- tropenol 3,3'-difluorobenzilate methobromide,
- scopine 3,3'- difluorobenzilate methobromide;
- tropenol 9-hydroxy-fluorene-9-carboxylate methobromide;
- tropenol 9-fluoro-fluorene-9-carboxylate methobromide;
- scopine 9-hydroxy-fluorene-9-carboxylate methobromide;
- scopine 9-fluoro-fluorene-9-carboxylate methobromide;
- tropenol 9-methyl-fluorene-9-carboxylate methobromide;
- scopine 9-methyl-fluorene-9-carboxylate methobromide;
- cyclopropyltropine benzilate methobromide;
- cyclopropyltropine 2,2-diphenylpropionate methobromide;
- cyclopropyltropine 9-hydroxy-xanthene-9-carboxylate methobromide;
- cyclopropyltropine 9-methyl-fluorene-9-carboxylate methobromide;
- cyclopropyltropine 9-methyl-xanthene-9-carboxylate methobromide;
- cyclopropyltropine 9-hydroxy-fluorene-9-carboxylate methobromide;
- cyclopropyltropine methyl 4,4'-difluorobenzilate methobromide.
- tropenol 9-hydroxy-xanthene-9-carboxylate methobromide;
- scopine 9-hydroxy-xanthene-9-carboxylate methobromide;
- tropenol 9-methyl-xanthene-9-carboxylate methobromide;
- scopine 9-methyl-xanthene-9-carboxylate methobromide;
- tropenol 9-ethyl-xanthene-9-carboxylate methobromide;
- tropenol 9-difluoromethyl-xanthene-9-carboxylate methobromide;
- scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
- (S)-fluoromethyl 6,9-difluoro-17-[(2-furanylcarbonyl)oxy]-11-hydroxy-16-methyl-3-oxo-androsta-1,4-diene-1 7-carbothionate
- (S)-(2-oxo-tetrahydro-furan-3S-yl)6,9-difluoro-11-hydroxy-16-methyl-3-oxo-17-propionyloxy-androsta-1,4-diene-1 7-carbothionate,
- cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and
- N-(3,5-dichloro-1-oxo-pyridin-4-yl)-4-difluoromethoxy-3-cyclopropylmethoxybenzamide
- (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
- (R)-(+)-1-(4-bromobenzyl)-4-[(3-cyclopentyloxy)-4-methoxyphenyl]-2-pyrrolidone
- 3-(cyclopentyloxy-4-methoxyphenyl)-1-(4-N'-[N-2-cyano-S-methylisothioureido]benzyl)-2-pyrrolidone
- cis[4-cyano-4-(3-cyclopentyloxy-4-methoxyphenyl)cyclohexane-1-carboxylic acid]
- 2-carbomethoxy-4-cyano-4-(3-cyclopropylmethoxy-4-difluoromethoxyphenyl)cyclohexan-1-one
- cis[4-cyano-4-(3-cyclopropylmethoxy-4-difluoromethoxyphenyl)cyclohexan-1-ol]
- (R)-(+)-ethyl[4-(3-cyclopentyloxy-4-methoxyphenyl)pyrrolidin-2-ylidene]acetate
- (S)-(−)-ethyl[4-(3-cyclopentyloxy-4-methoxyphenyl)pyrrolidin-2-ylidene]acetate
- 9-cyclopentyl-5,6-dihydro-7-ethyl-3-(2-thienyl)-9H-pyrazolo[3,4-c]-1,2,4-triazolo[4,3-a]pyridine
- 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropyl-methoxy-quinazoline 4-[(3-chloro-4-fluorophenyl)amino]-6-{[4-(N,N-diethylamino)-1-oxo-2-buten-1-yl]amino}-7-cyclopropyl-methoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]-amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)ethoxy]-7-methoxy-quinazoline 4-[(3-chloro-4-fluorophenyl)amino]-6-({4-[N-(2-methoxy-ethyl)-N-methylamino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropyloxy-quinazoline 4-[(R)-(1-phenyl-ethyl)amino]-6-({4-[N-(tetrahydropyran-4-yl)-N-methylamino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methylamino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6,7-bis-(2-methoxy-ethoxy)-quinazoline 4-[(3-chloro-4-fluorophenyl)amino]-7-[3-(morpholin-4-yl)-propyloxy]-6-[(vinylcarbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)ethoxy]-7-methoxy-quinazoline 4-[(3-chloro-4-fluoro-phenyl)amino]-6-[2-(2,2-dimethyl-6-oxo-morpholin-4-yl)ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylaminocyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxyquinazoline 4-[(3-chloro-4-fluoro-phenyl)amino]-6-((S)-tetrahydrofuran-3-yloxy)-7-hydroxyquinazoline 4-[(3-chloro-4-fluoro-phenyl)amino]-6-(tetrahydropyran-4-yloxy)-7-(2-methoxyethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxyacetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxyethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

It is also possible to use inhalable macromolecules as disclosed in EP 1 003 478 A1 or CA 2297174 A1.

In addition, the compound may come from the group of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

List of Reference Numerals

| | |
|---|---|
| 1 | inhaler |
| 2 | formulation |
| 3 | reservoir |
| 4 | dosing device |
| 5 | delivery channel |
| 6 | outlet |
| 7 | dosing chamber |
| 8 | wall |
| 9 | supply line |
| 10 | supply chamber |
| 11 | pump device |
| 12 | pump piston |
| 13 | pump chamber |
| 14 | actuating device |
| 15 | spring |
| 16 | piston |
| 17 | piston guide |
| 18 | valve device |
| 19 | communication channel |
| 20 | first connecting channel |
| 21 | second connecting channel |
| 22 | supply air channel |
| 23 | restoring spring |
| 24 | dosing chamber part |
| 25 | dosing chamber part |
| 26 | dosing chamber part |

The invention claimed is:

1. Dosing device (4) for an inhaler (1) for dosing a small amount of a powdered formulation (2), comprising a reservoir (3) for the formulation (2) and a dosing chamber (7) for receiving the formulation (2) supplied from the reservoir (3), wherein the dosing chamber (7) has a wall (8) that is gas-permeable at least in part, so that the formulation (2) can be taken into the dosing chamber (7) by underpressure and can be expelled from the dosing chamber (7) by overpressure, characterised in that the dosing device (4) comprises a pump device (11) for alternately generating the underpressure for taking the formulation (2) into the dosing chamber (7) and the overpressure for expelling the formulation (2) from the dosing chamber (7).

2. Dosing device according to claim 1, characterised in that the pump device (11) can be operated manually.

3. Dosing device (4) according to claim 1 wherein the dosing device (4) comprises a piston (16) that carries or forms the dosing chamber (7), which is movable between an uptake position for taking the formulation (2) into the dosing chamber (7) and an expulsion position for expelling the formulation (2) from the dosing chamber (7).

4. Dosing device according to claim 3, characterised in that the piston (16) forms the pump device (11) or is coupled thereto.

5. Dosing device according to claim 3, characterised in that the piston (16) forms and/or controls a valve device (18) of the pump device (11).

6. Dosing device according to claim 3, characterised in that the dosing device (4) comprises a common actuating device (14) for the piston (16) and the pump device (11).

7. Dosing device according to claim 3, characterised in that the piston (16) can be operated manually.

8. Dosing device according to claim 3, characterised in that the piston (16) extends through the reservoir (3).

9. Dosing device according to claim 3, characterised in that associated with the piston (16) is a device for loosening the formulation (2) in the reservoir (3) during the movement of the piston (16).

10. Dosing device according to claim 9, characterised in that the dosing device (4) has a spring (23) associated with the piston (16) for returning the piston (16) to its uptake or delivery position.

11. Dosing device according to claim 10, characterised in that the spring (23) forms the loosening device.

12. Dosing device according to claim 10, characterised in that the spring (23) surrounds the piston (16).

13. Dosing device according to claim 10, characterised in that the spring (23) extends into or through the reservoir (3).

14. Dosing device according to claim 3, characterised in that the piston (16) is of hollow construction, at least in parts, or is provided with a communication channel (19) to make it possible to generate or control the underpressure and/or overpressure in the dosing chamber (7).

15. Dosing device (4) according to claim 1, wherein the dosing chamber (7) is adjustable in size.

16. Dosing device according to claim 15, characterised in that the dosing device (4) has at least two dosing chamber parts (24, 25, 26) that can be moved relative to one by screwing or turning.

17. Dosing device according to claim 16, characterised in that the two dosing chamber parts (24, 25, 26) can be screwed axially into one another.

18. Dosing device according to claim 16, characterised in that one dosing chamber part (25) is porous and/or sleeve-like in construction and is covered by the other dosing chamber part (24, 26), the degree of overlap being variable.

19. Dosing device according to claim 15, characterised in that the dosing device (4) has a piston (16) which carries or forms the dosing chamber (7).

20. Method of dosing a small amount of a powdered formulation (2) in an inhaler (1), wherein a dosing chamber (7) with a wall (8) that is gas-permeable in parts is filled with the formulation (2) by underpressure and then the formulation (2) is expelled again from the dosing chamber (7) by overpressure, characterised in that the underpressure and the overpressure is produced by:

(a) a pump device (11), and (b) the dosing chamber (7), wherein the dosing chamber (7) is moved between an uptake position for taking up the formulation (2) and a delivery position for dispensing the formulation (2) and the movement and/or arrival at the uptake position and/or the delivery position controls the underpressure and/or overpressure acting in the dosing chamber (7).

* * * * *